(12) United States Patent
Morikoshi et al.

(10) Patent No.: US 8,999,374 B2
(45) Date of Patent: Apr. 7, 2015

(54) METHOD OF INHIBITING SALMONELLA IN LIVESTOCK AND POULTRY

(75) Inventors: Toshimichi Morikoshi, Kuroiso (JP); Futoshi Yokomizo, Izumisano (JP)

(73) Assignee: Fuji Oil Co., Ltd., Osaka (JP)

( * ) Notice: Subject to any disclaimer, the term of this patent is extended or adjusted under 35 U.S.C. 154(b) by 2714 days.

(21) Appl. No.: 10/536,488

(22) PCT Filed: Nov. 26, 2003

(86) PCT No.: PCT/JP03/15092
§ 371 (c)(1),
(2), (4) Date: Nov. 14, 2005

(87) PCT Pub. No.: WO2004/048587
PCT Pub. Date: Jun. 10, 2004

(65) Prior Publication Data
US 2006/0073191 A1    Apr. 6, 2006

(30) Foreign Application Priority Data

Nov. 26, 2002    (JP) .................................. 2002-342892

(51) Int. Cl.
| | | |
|---|---|---|
| *A23K 1/17* | (2006.01) |
| *A23K 1/18* | (2006.01) |
| *A23K 1/165* | (2006.01) |
| *A61K 47/00* | (2006.01) |
| *A61K 36/899* | (2006.01) |
| *A01N 65/00* | (2009.01) |
| *A23K 1/16* | (2006.01) |
| *A23L 1/0528* | (2006.01) |
| *A61K 31/7016* | (2006.01) |
| *C07H 3/04* | (2006.01) |
| *C12P 19/12* | (2006.01) |
| *C12P 19/14* | (2006.01) |

(52) U.S. Cl.
CPC ............. *A23K 1/1826* (2013.01); *A23K 1/1643* (2013.01); *A23L 1/0528* (2013.01); *A61K 31/7016* (2013.01); *C07H 3/04* (2013.01); *C12P 19/12* (2013.01); *C12P 19/14* (2013.01); *Y10S 424/823* (2013.01); *Y10S 424/826* (2013.01)

(58) Field of Classification Search
None
See application file for complete search history.

(56) References Cited

U.S. PATENT DOCUMENTS 6,896,918 B2 * 5/2005 Yokomizo ....................... 426/52

FOREIGN PATENT DOCUMENTS

| JP | 63-209595 A | 8/1988 |
| JP | 7-236429 A | 9/1995 |
| JP | 11-18793 A | 1/1999 |
| JP | 2000-245357 A | 9/2000 |
| JP | 2001-231591 A | 8/2001 |
| WO | WO02/052947 | 7/2002 |

OTHER PUBLICATIONS

Kusakabe, I. et al., Preparation of β-1, 4 - Mannobiose from White Copra Meal by a Mannanase from *Penicillum purpurogenum*, Agric. Biol. Chem. (1987), vol. 51, No. 10, pp. 2825-2826.
Supplementary European Search Report for a corresponding Foreign counterpart application EP 03775906 issued on Dec. 2, 2008.

* cited by examiner

*Primary Examiner* — Debbie K Ware
(74) *Attorney, Agent, or Firm* — Locke Lord, LLP

(57) ABSTRACT

The present invention is to provide a β-1,4-mannobiose-containing composition which can inhibit colonization of *salmonella* in animal body and effectively excrete *salmonella* outside the body and the method for producing thereof, a feed additive containing the β-1,4-mannobiose-containing composition, and a feed blended with the β-1,4-mannobiose-containing composition. The present invention is intended to provide a method for producing the β-1,4-mannobiose-containing composition wherein a mannan degrading enzyme is functioned to a mannan-containing natural material for producing at least 10% by weight of β-1,4-mannobiose based on the mannan before the degradation, the β-1,4-mannobiose-containing composition prepared through the function of a mannan degrading enzyme to a mannan-containing natural material, which contains at least 10% by weight of β-1,4-mannobiose in terms of dry matter, a feed additive containing the β-1,4-mannobiose-containing composition, and a feed blended with the β-1,4-mannobiose-containing composition.

5 Claims, 3 Drawing Sheets

METHOD OF INHIBITING SALMONELLA IN LIVESTOCK AND POULTRY

This is a national phase application to which priority under 35 U.S.C. §371 of international application Serial No. PCT/JP2003/015092, filed Nov. 26, 2003 is claimed, which claims the benefit of Japanese Patent No. JP2002/342892, filed on Nov. 26, 2002.

TECHNICAL FIELD

The present invention relates to a β3-1,4-mannobiose-containing composition and the method for producing thereof, a feed additive containing the β-1,4-mannobiose-containing composition and a feed blended with the β-1,4-mannobiose-containing composition, particularly a feed which can inhibit colonization of *salmonella* in intestine of livestock or poultry.

BACKGROUND ART

Conventionally, it has been known that mannan whose constituent sugar is mannose is contained abundantly in palm kernel meal, copra meal, guar meal, and soon, and various methods for producing mannose, mannooligosaccharide and mannose polysaccharides through the function of enzymes to these natural materials have been proposed. Further, such feeds supplemented with mannoses have been known to have the effect of excreting bacteria outside the body (the effect of inhibiting colonization of *salmonella* ) for inhibiting the colonization of harmful bacteria i.e. *salmonella* in intestine, and various techniques using this effect have been proposed (Poultry Science, 68, p. 1357, 1989).

For instance, it has been reported that a feed which are prepared by degrading materials containing mannan such as guar meal and copra meal and contains mannobiose and mannotriose as major components where mannooligosacchrides mixed with monosaccharides are blended, can improve the quality of egg of layer. It has been reported, in the meantime, that mannooligosaccharides may be useful in preventing colonization of *salmonella* in intestine of livestock (Japanese Laid-Open Patent Application No. 1995-236429). It has also been reported that a feed blended with mannose, methyl-α-mannoside, mannooligosaccharide, enzyme of mannan prepared from guar gum, locust bean gum or yeast and/or mannoses such as hydrolysate by acid is/are useful in prevention of harmful bacterial infection such as by *salmonella* (Japanese Laid-Open Patent Application No. 1996-38064). Further, it has been reported that a feed for livestock blended with mannose-based polysaccharide which mainly contains polysaccharide (30-80%) having 40-100 repeating units of mannose, which also contains oligosaccharide (5-30%), is effective in prevention of colonization of *salmonella* in intestine of livestock (Japanese Laid-Open Patent Application No. 1996-173055). Besides, a feed blended with degraded product into mannooligosaccharide through the function of enzymes to mannan-rich materials such as palm kernel meal and guar meal, a feed containing mannose prepared through the function of enzymes to copra meal, and a method for producing mannose and/or mannooligosccharide using palm kernel meal have been reported (International Application Published under PCT Nos. 95/17103 and 99/08544, and Japanese Laid-Open Patent Application No. 2001-231591).

Various proposals have been made as mentioned above, but the effect of inhibiting colonization of *salmonella* in intestine of livestock is still so far from satisfactory sufficient in the present situation that additional modification has been desired. For instance, it has been known that though mannose has an effect of inhibiting colonization of *salmonella* (an effect of eliminating *salmonella* ), even if mannose is given to livestock as feed, most of it is easily assimilated by intestinal bacteria and so on, as it being a simple sugar, and it may also be assumed that mannose is digested, absorbed, and excreted by the livestock itself. Further, the result of the experiment by the present inventors provide the knowledge that supplement of a probiotic for enhancing immunity of livestock will further increase mannose-degrading activity and cause the most part of mannose given as a measure for fighting against *salmonella* to be absent. Accordingly, an extremely large amount of mannose should be administered to actually achieve a sufficient effect of inhibiting colonization of *salmonella* . On the other hand, knowledge was acquired through the agglutination test using yeast that effects of inhibiting colonization of *salmonella* by mannooligosaccharide and mannose-based polysaccharide whose molecular weights are larger than that of mannobiose are less significant. The present invention was made in view of the current condition. The object of the present invention is to provide a β-1,4-mannobiose-containing composition which can inhibit colonization of *salmonella* in animal body and effectively excrete *salmonella* outside the body and the method for producing thereof, a feed additive containing the β-1,4-mannobiose-containing composition, and a feed blended with the β-1,4-mannobiose-containing composition.

As a result of intensive search, the present inventors acquired knowledge that β-1,4-mannobiose can work more effectively than mannose does in inhibiting colonization of *salmonella* , since β-1,4-mannobiose has a *salmonella* -recognition ability and it is difficult to be assimilated by intestinal bacteria of livestock, though its *salmonella* -recognition ability is slightly inferior to that of mannose. Hence, establishing an efficient method for producing a β-1,4-mannobiose-containing composition and finding that the prepared β-1,4-mannobiose-containing composition has β-1,4-mannobiose at high content, the present inventors completed the present invention.

DISCLOSURE OF THE INVENTION

The present invention relates to: a method for producing a β-1,4-mannobiose-containing composition wherein a mannan degrading enzyme is functioned to a mannan-containing natural material to produce at least 10% by weight of β-1,4-mannobiose based on the mannan before the degradation ("1"); the method for producing a β-1,4-mannobiose-containing composition wherein a mannan degrading enzyme is functioned to mannan extracted from a mannan-containing natural material to produce at least 10% by weight of β-1,4-mannobiose based on the mannan before the degradation ("2"); the method for producing a β-1,4-mannobiose-containing composition according to "1" or "2" wherein a mannan degrading enzyme is functioned to 100 parts by weight of mannan with supplementing 50-10000 parts by weight of water ("3"); the method for producing a β-1,4-mannobiose-containing composition according to any one of "1" to "3" wherein the temperature at which the mannan degrading enzyme is functioned ranges from 40° to 55° C. ("4"); the method for producing a β-1,4-mannobiose-containing composition according to any one of "1" to "4" wherein 20-80% by weight of β-1,4-mannobiose based on the mannan before the degradation is produced ("5"); and the method for producing a β-1,4-mannobiose-containing composition according to any one of "1" to "5" wherein the mannan-containing natural material is palm kernel meal and/or copra meal ("6").

The present invention also relates to a feed additive containing the β-1,4-mannobiose-containing composition prepared by the method for producing according to any one of "1" to "6" ("7"); a feed blended with the β-1,4-mannobiose-containing composition prepared by the method for producing according to any one of "1" to "7", which can inhibit colonization of *salmonella* in intestine of livestock or poultry ("8"); the feed according to "8", in which 0.001-1% by weight of β-1,4-mannobiose is contained ("9"); the β-1,4-mannobiose-containing composition prepared through the function of a mannan degrading enzyme to a mannan-containing natural material, which contains at least 3% by weight of β-1,4-mannobiose in terms of dry matter ("10"); the β-1,4-mannobiose-containing composition prepared through the function of a mannan degrading enzyme to mannan extracted from a mannan-containing natural material, which contains at least 10% by weight of β-1,4-mannobiose in terms of dry matter (11); the β-1,4-mannobiose-containing composition according to "10" or "11" wherein the mannan-containing natural material is palm kernel meal and/or copra meal (12); a feed additive which contains the β-1,4-mannobiose-containing composition according to any one of "10" to "12" ("13"); a feed blended with the β-1,4-mannobiose-containing composition according to any one of "10" to "12", which can inhibit colonization of *salmonella* in intestine of livestock or poultry ("14"); and the feed according to "14" which contains 0.001-1% by weight of β-1,4-mannobiose ("15").

BEST MODE OF CARRYING OUT THE INVENTION

Figure 1:
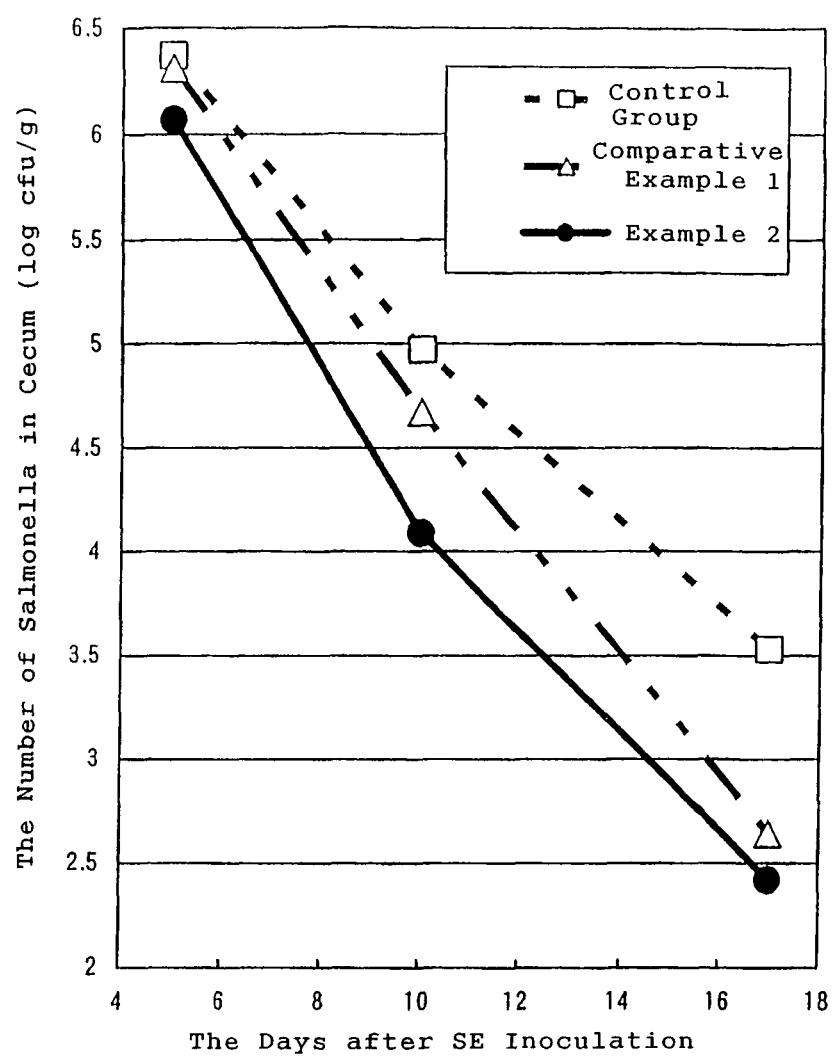
FIG. 1 is a graph showing the number of *salmonella* in cecum with respect to the days after inoculation of *salmonella* in newly hatched male chicks of layers given a feed according to the present invention, a feed according to the Comparative Example 1, and a commercially available feed.

As the method for producing the β-1,4-mannobiose-containing composition of the present invention, it is not especially limited to as long as it is a method for producing at least 10% by weight (10-100% by weight) of β-1,4-mannobiose based on the mannan before the degradation through the function of a mannan degrading enzyme to a mannan-containing natural material and hydrolysis or the like of mannan in the mannan-containing natural material, or a method for producing at least 10% by weight of β-1,4-mannobiose based on the mannan before the degradation through the function of a mannan degrading enzyme to mannan extracted from a mannan-containing natural material, but it is preferable to produce 20-80% by weight of β-1,4-mannobiose based on the mannan before the degradation, and it is more preferable to produce 30-80% by weight of β-1,4-mannobiose based on the mannan before the degradation.

As for the β-1,4-mannobiose-containing composition of the present invention, it is not especially limited to as long as it is a β-1,4-mannobiose-containing composition prepared through the function of a mannan degrading enzyme to a mannan-containing natural material and containing at least 3% by weight of β-1,4-mannobiose in terms of dry matter, and a β-1,4-mannobiose-containing composition prepared through the function of a mannan degrading enzyme to mannan extracted from a mannan-containing natural material and containing at least 10% by weight of β-1,4-mannobiose in terms of dry matter. Such β-1,4-mannobiose-containing composition can be produced e.g. by the aforementioned method for producing a β-1,4-mannobiose-containing composition of the present invention.

As the feed additive of the present invention, it is not especially limited to as long as it is the β-1,4-mannobiose-containing composition prepared by the aforementioned method for producing the β-1,4-mannobiose-containing composition of the present invention, and a feed additive containing the aforementioned β-1,4-mannobiose-containing composition of the present invention. As such feed additives, a feed additive comprising these β-1,4-mannobiose-containing compositions and these β-1,4-mannobiose-containing compositions blended with other additive components such as preservative, can be exemplified.

Further, as for the usage pattern of the aforementioned β-1,4-mannobiose-containing composition and feed additive, an enzyme treated substance per se and the dry substance thereof, or an extract prepared by extracting mannobiose with water or the like after enzymic treatment and the dry substance thereof can be exemplified but it is not especially limited to these exemplifications.

As for the aforementioned mannan-containing natural material, it is not especially limited to as long as it contains mannose with the β-1,4 bond, for instance, mannan from higher plant such as copra meal, palm kernel meal, guar meal and the like can be exemplified, and copra meal and palm kernel meal are preferable considering that they are readily available and mannan-rich. Further, as for a method for extracting mannan insoluble in water from a mannan-containing natural material by producing micelle, methods for extracting with alkaline solution, e.g. a 5% cold sodium hydroxide solution or a 10% sodium hydroxide solution can be exemplified.

As for the mannan degrading enzyme used herein, it is not especially limited to as long as it has an activity to degrade mannan such as mannanase, mannosidase, hemicellulase and the like to produce β-1,4-mannobiose or it has an activity to synthesize β-1,4-mannobiose from mannose produced from mannan, while besides those derived from Aspergillus niger and commercially available, for instance Hemicellulase GM "AMANO" (Amano Pharmaceutical Co., Ltd.), Sumizymes ACH and ACH-L (Shin Nihon Chemical Co., Ltd.), Cellulosin GM5 (Hankyu Bioindustry Co., Ltd.) and the like can be preferably used, those commercially available as xylanase or cellulase may be used when it has the hydrolytic activity, for instance, Cellulase Y-NC (Yakult Pharmaceutical Co., Ltd.) and the like can be used. Among them, enzymes having a low mannosidase (exo-type) activity and a high mannanase (endo-type) activity are preferable; specifically, Hemicellulase GM "AMANO" (Amano Pharmaceutical Co., Ltd.), Sumizymes ACH and ACH-L (Shin Nihon Chemical Co., Ltd.) are preferable as their use can produce mannobiose in large amount as well as inhibit mannose production. As such, being more convenient, the method for degrading β-1,4-mannan is more preferable in view of resourcefulness and reaction efficiency of the material, although β-1,4-mannobiose can be prepared not only by the method for degrading β-1,4-mannan but also by the method for synthesizing it from mannose.

In the production of the β-1,4-mannobiose-containing composition of the present invention, a mannan degrading enzyme is functioned to a mannan-containing natural material or mannan extracted from a mannan-containing natural material, while it is preferable to use an enzymic solution in which the mannan degrading enzyme is dissolved or dispersed in water. In order to perform efficient reaction, water adjustment is required in reaction system consisting of a mannan-containing natural material or mannan, a mannan degrading enzyme and water. As for water loading for water adjustment, 50-10000 parts by weight of water based on 100 parts by weight of mannan is preferable, and water of 100-1500 parts by weight based on 100 parts by weight of mannan is more preferable. Setting water loading in the aforementioned range enables sufficient amount of water to exist in the reaction system, fibers of mannans to swell sufficiently for enzymic solution to contact easily, and mannobiose to be produced effectively. Further, setting the aforementioned range can inhibit the decrease of reaction efficiency accompanied by dilution of enzyme concentration caused by excessive water as well as the increase of cost for drying in the dry process. Additionally, as for the amount of enzyme and reaction time, there is no limitation as long as mannobiose to be produced is at least 10% by weight based on the mannan before the degradation, while it is preferable not to make the reaction time be longer than necessary because even when the enzyme having high mannanase (endo-type) activity is used, mannobiose is degraded since the enzyme usually has mannosidase (exo-type) activity as well. Meanwhile, reaction temperature preferably ranges from 40° to 65° C., but the higher it rises the more the activity of mannosidase enhances and the more the amount of production of mannose increases. Therefore, when it is desired to inhibit mannose production as well as to produce mannobiose in large amount, the reaction may be performed at 40° to 55° C., or more preferably at 45° to 53° C.

For instance, reaction for 3-36 hours using palm kernel meal (mannan content is approximately 36% by weight) as a material can produce approximately cup to 6-17 parts by weight of β-1,4-mannobiose content based on 100 parts by weight of material, depending on type and amount of used enzyme and time to use enzyme. Among the β-1,4-mannobiose-containing compositions prepared by the method for producing a β-1,4-mannobiose-containing composition of the present invention, it is preferable for a feed additive and a feed when the β-1,4-mannobiose-containing compositions contain at least 3% by weight of β-1,4-mannobiose in term of dry matter, and it is more preferable when they contain 10% by weight or more of β-1,4-mannobiose in term of dry matter.

The β-1,4-mannobiose-containing composition of the present invention is particularly effective because it can be used as a feed additive for inhibiting colonization of *salmonella* in intestine of livestock or poultry and it is difficult to be assimilated when it is used with a probiotic such as bacteria present in the adult chicken cecal for enhancing immunity of livestock. The β-1,4-mannobiose-containing composition can be used e.g. as a feed as it is, and a feed can be supplemented with it as well. This β-1,4-mannobiose-containing composition contains mannose, mannooligosaccharides and the like besides mannobiose, while it is not particularly necessary to extract and purify mannobiose exclusively, rather it is preferable to include mannose, mannooligosaccharides and the like. When a feed is supplemented with the β-1,4-mannobiose-containing composition, it is preferable to be supplemented to contain 0.001-1% by weight of mannobiose therein, and it is more preferable to be supplemented to contain 0.005-0.1% by weight of mannobiose therein. The effect of the present invention can be more successful as the mannobiose content falls within the aforementioned range. Meanwhile, when the β-1,4-mannobiose-containing composition is distributed and used as it is e.g. for a feed additive, concern about occurrence of mold or bacteria is inevitable, so the β-1,4-mannobiose-containing composition is preferably dried in order that its water content is reduced to 10% by weight or less by the method with a fluidized bed dryer or of vacuum dehydration.

As for the feed which can inhibit colonization of *salmonella* of the present invention, it is not especially limited to as long as it is the β-1,4-mannobiose-containing composition prepared by the aforementioned method for producing a β-1,4-mannobiose-containing composition of the present invention, and a feed blended with the aforementioned β-1,4-mannobiose-containing composition of the present invention. Giving the feed of the present invention in solid or liquid form to livestock or poultry can inhibit colonization of *salmonella* in animal body to effectively excrete *salmonella* outside the body. β-1,4-mannobiose can work more effectively than mannose does in inhibiting colonization of *salmonella* and effectively excrete the *salmonella* outside the body, since β-1,4-mannobiose is difficult to be assimilated by intestinal bacteria of livestock, though its recognition ability is slightly inferior to that of mannose. Therefore it allows smaller content of mannoses in feed, leading to the great reduction of economic burden.

The present invention will be described in more detail by showing the Examples in the following; the present invention is not limited to these following Examples. In the Examples, "part" and "%" represent "part by weight" and "% by weight" respectively unless otherwise specified.

EXAMPLE 1

Production of a β-1,4-Mannobiose-containing Composition from Palm Kernel Meal 150 parts of enzymic solution, in which 0.25 parts of enzyme Hemicellulase GM "AMANO" (Amano Pharmaceutical Co., Ltd.) was dissolved, was functioned to 100 parts of palm kernel meal (FUJI OIL Co., Ltd.) containing mannan at 36% and water at 8.2% for 12 hours at 60° C., and then the solution was dried with a fluidized bed dryer (OKAWARA MFG. Co., Ltd.) until its water content reduced to 9.8% to yield 102 parts of dry powder. When the mannose content and β-1,4-mannobiose content in this dry powder were measured by ion-exchange chromatography, it was found that 1.44 parts of mannose and 10.58 parts of β-1,4-mannobiose (29.4% based on mannan; 11.5% in terms of dry matter) were produced.

EXAMPLE 2

Production of a β-1,4-Mannobiose-containing Composition from Copra Meal 150 parts of enzymic solution, in which 0.25 parts of enzyme Hemicellulase GM "AMANO" (Amano Pharmaceutical Co., Ltd.) was dissolved, was functioned to 100 parts of copra meal containing mannan at 30% and water at 4.2% for 12 hours at 60° C., and then the solution was dried with a fluidized bed dryer until its water content reduced to 9.3% to yield 106 parts of dry powder. When the mannose content and β-1,4-mannobiose content in this dry powder were measured, it was found that 1.36 parts of mannose and 12.35 parts of β-1,4-mannobiose (41.2% based on mannan; 12.9% in terms of dry matter) were produced.

COMPARATIVE EXAMPLE 1

150 parts of enzymic solution, in which 0.3 parts of enzyme Cellulosin GM 5 (Hankyu Bio Industry Co., Ltd.) was dissolved, was functioned to 100 parts of palm kernel meal containing mannan at 36% and water at 8.2% for 72 hours at 60° C., and then the solution was dried with a fluidized bed dryer until its water content reduced to 7.8% to yield 100 parts of dry powder. When the mannose content and β-1,4-mannobiose content in this dry powder were measured, it was found that 11.52 parts of mannose and 2.57 parts of β-1,4-mannobiose (7.14% based on mannan; 2.79% in terms of dry matter) were produced.

EXAMPLE 3

Inhibition Test of Salmonella/Yeast Agglutination

Inhibition tests of salmonella agglutination were carried out on various saccharides as follows. 0.1 ml of suspension of Salmonella enteritidis (Salmonella enteritidis KTE-61 strain isolated at ITOCHU FEED MILLS Co., Ltd., the number of bacteria is $1\times10^8$ cfu/ml) was well mixed with 0.1 ml of distilled water, and then 0.1 ml of suspension of yeast Candida albicans (Candida albicans KI-102001 purchased from Japanese Association of Veterinary Biologics) was added into and mixed with the solution. Preliminary test was carried out for observing by stereoscopic microscope (OLYMPUS Co., Ltd) that agglutination occurs in this liquid mixture.

After 0.5 g of dry powder yielded in Example 1 was mixed into and suspended in 5 ml of water, the solution was centrifuged at 10000 rpm for 5 minutes, and approximately 10 mg of β-1,4-mannobiose was taken by high performance liquid chromatography (Nihon Bunko Co., Ltd.) from centrifuge supernatant. Next, in a similar manner to the aforementioned preliminary test, with the use of aqueous solution of saccharide where the aforementioned taken β-1,4-mannobiose and a mannose reagent (D-Mannose; Wako Pure Chemical Industries, Ltd.) were used instead of distilled water, the minimum concentration for inhibiting agglutination of liquid mixture (the minimum concentration for inhibiting agglutination) was obtained by varying the concentration, respectively. The actual minimum concentration for inhibiting the agglutination in liquid mixture and the relative concentration (ratio of concentration) when the minimum concentration for inhibiting agglutination of mannose is set 1 are shown in table 1. As it is apparent from Table 1, it was revealed that β-1,4-mannobiose in a quantity of approximately twice as large as mannose is necessary for inhibiting agglutination by salmonella.

TABLE 1

| | Actual Concentration (µg/ml) | Relative Concentration (Based on Mannose) |
|---|---|---|
| Mannose (D-Mannose) | 594 | 1.000 |
| Mannobiose | 1290 | 2.173 |

EXAMPLE 4

Metabolism Test

Water was added into the dry powders yielded in Examples 1 and 2 and Comparative Example 1 respectively to make suspensions having ten times the amount of the dry powders. Additionally, 1% aqueous solution of a mannose reagent was prepared. Inteclean (ITOCHU FEED MILLS Co., Ltd.), a culture of chicken cecal content was inoculated into abovementioned four liquid of suspensions or aqueous solution to examine mannose metabolism and β-1,4-mannobiose metabolism at 37° C. The suspensions or the aqueous solution at beginning of culture and 20 hours after the beginning of culture were sampled and the sample was subjected centrifuge at 10000 rpm for 10 minutes. Then, the supernatants of them were examined with respect to contents (mg/g) of respective components by ion-exchange chromatography, the result of which is shown in Table 2. As it is apparent from Table 2, in Comparative Example 1, the quantity of mannose was reduced by 66%, while that of mannose reagent was reduced by 69%, which reveals that mannose is metabolized by intestinal bacteria very easily. On the other hand, reduced quantity of β-1,4-mannobiose in Examples 1 and 2 were 16% and 17%, respectively, which reveals that metabolic rate of β-1,4-mannobiose is apparently lower than that of mannose.

TABLE 2

| | At Culture Beginning (mg/g) | | After 20 h Anaerobic Culture (mg/g) | |
|---|---|---|---|---|
| | Mannose | Mannobiose | Mannose | Mannobiose |
| Example 1 | 1.88 | 10.91 | 0.03 | 9.15 |
| Example 2 | 1.76 | 12.15 | 0 | 10.03 |
| Comparative Example 1 | 10.45 | 2.53 | 3.57 | 2.12 |
| Mannose 1% | 9.45 | 0 | 2.93 | 0 |

From the results of above agglutination test and metabolism test, it is shown that β-1,4-mannobiose can work more effectively than mannose does in inhibiting colonization of salmonella and effectively excrete the salmonella outside the body, since β-1,4-mannobiose is difficult to be assimilated by intestinal bacteria of livestock, though its salmonella recognition ability is slightly inferior to that of mannose. Further, the result of the metabolism test shows that β-1,4-mannobiose is particularly useful when used with a probiotic such as adult chicken cecal content for enhancing immunity of livestock because it is difficult to be assimilated.

EXAMPLE 5

Animal Test 150 of newly hatched male chicks of commercial layers were divided into three groups in total. The three groups consist of a control group of 50 chicks given a commercial blended feed for commercial broiler chicken (trade name: AMATAKE S, agent free/ITOCHU FEED MILLS Co., Ltd.), a group of 50 chicks given a feed prepared by supplementing 0.1% of the dry powder yielded in Example 2 with the blended feed, and a group of 50 chicks given a feed prepared by supplementing 0.1% of the dry powder yielded in Comparative Example 1. The chicks were raised with continuous feeding and voluntary water-drinking. The chicks were orally inoculated with salmonella (Salmonella enteritidis KTE-61 strain) by $3.9 \times 10^8$ cfu per a chick at the age of day three. The number of *salmonella* (log) in their cecal content with respective groups was examined on days 5, 10 and 17 from the *salmonella* inoculation. The result is shown in Table 3, while FIG. 1 graphically illustrates it.

TABLE 3

|  | 5 Days from SE Inoculation (log cfu/g) | 10 Days from SE Inoculation (log cfu/g) | 17 Days from SE Inoculation (log cfu/g) |
| --- | --- | --- | --- |
| Control Group (Additive Free) | 6.37 | 4.97 | 3.53 |
| Comparative Example 1 (Enzymatically Treated Palm Kernel Meal, Mannose-Type) | 6.31 | 4.67 | 2.64 |
| Example 2 (Enzymatically Treated Copra Meal, β-Mannobiose-Type) | 6.07 | 4.09 | 2.42 |

As it is apparent from Table 3 and FIG. 1, it was revealed that the number of *salmonella* in the both groups one of which was a group given the feed prepared by supplementing with the dry powder yielded in Example 2 and the other was a group given the feed prepared by supplementing with the dry powder yielded in Comparative Example 1, were smaller than that in the control group all through the testing period, so that *salmonella* were effectively reduced in those groups. Particularly, the group given the feed prepared by supplementing with the dry powder yielded in Example 2 showed smaller number of *salmonella* than that of the group given the feed prepared by supplementing with the dry powder yielded in Comparative Example 1, which indicates that the feed prepared by supplementing with the dry powder yielded in Example 2 functions more effectively.

EXAMPLE 6

Production of a β-1,4-Mannobiose-containing Composition from Copra Meal 125 parts of enzymic solution in which 0.25 parts of enzyme Sumizyme ACH (Shin Nihon Chemical Co., Ltd.) was dissolved, was functioned to 100 parts of copra meal at 50° C. for 22 hours, and then the solution was dried with a fluidized bed dryer until its water content reduced to 7.1% to yield 103 parts of dry powder. It was found that 1.17 parts of mannose and 14.18 parts of mannobiose (47.3% based on mannan) were produced in this dry powder.

COMPARATIVE EXAMPLE 2

150 parts of enzymic solution in which 0.3 parts of enzyme Cellulosin GM5 (Hankyu Bio Industry Co., Ltd.) was dissolved, was functioned to 100 parts of copra meal at 60° C. for 72 hours, and then the solution was dried with a fluidized bed dryer until its water content reduced to 6.4% to yield 100 parts of dry powder. It was found that 13.72 parts of mannose and 0.64 parts of mannobiose (2.13% based on mannan) were produced in this dry powder.

EXAMPLE 7

Animal Test 2, Effect on Broiler Chick 45 of newly hatched chicks of commercial broilers were divided into three groups in total. The three groups consist of a control group of 15 chicks given a commercial blended feed for commercial broiler chicken (trade name: AMATAKE S, agent free/ITOCHU FEED MILLS Co., Ltd.), a group of 15 chicks given a feed prepared by supplementing 0.1% of the dry powder yielded in Example 6 with the blended feed, and a group of 15 chicks given a feed prepared by supplementing 0.1% of the dry powder yielded in Comparative Example 2. The chicks were preliminary raised for one week with continuous feeding and voluntary water-drinking. The chicks were then orally inoculated with *salmonella* (*Salmonella enteritidis* HY-1 strain) by $2.27 \times 10^7$ cfu per a chick at the age of week one. The number of *salmonella* (log) in their cecal content with the respective groups was examined at weeks one, two and three from the *salmonella* inoculation by dissecting 5 chicks of the respective groups.

Figure 2:
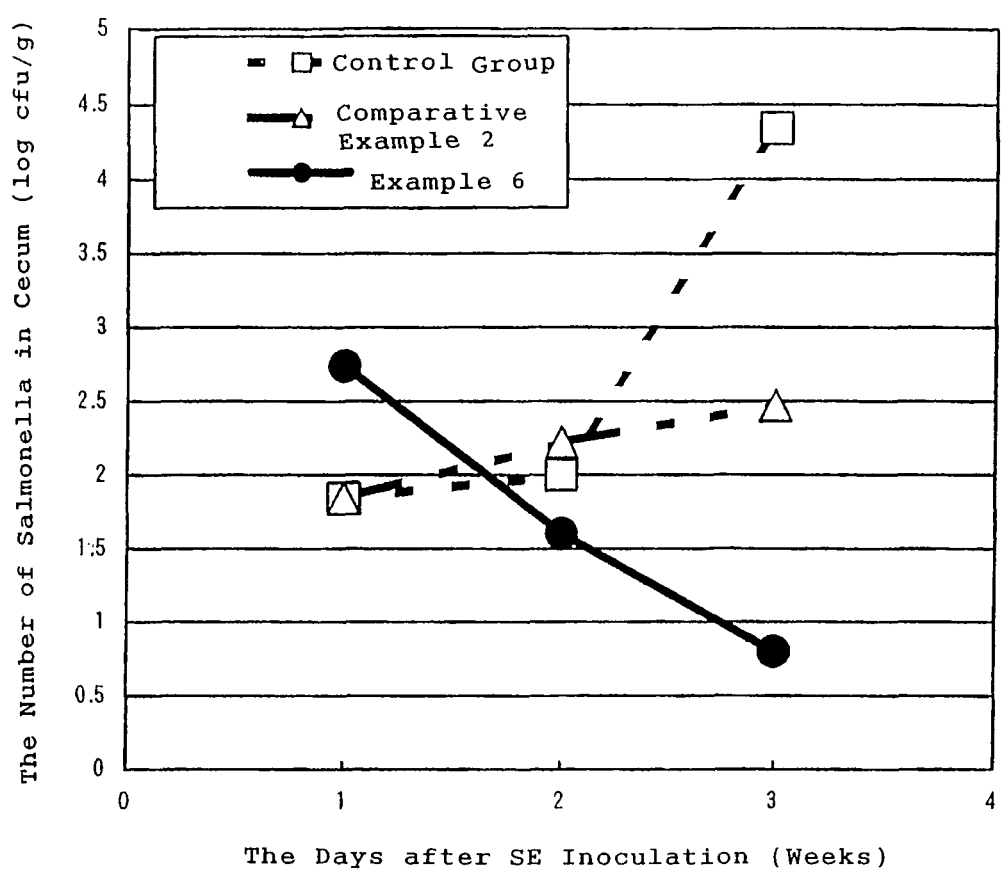
FIG. 2 is a graph showing the number of *salmonella* in cecum with respect to the days after inoculation of *salmonella* in newly hatched chicks of broiler given a feed according to the present invention, a feed according to the Comparative Example 2, and a commercially available feed.

The result is shown in Table 4, while FIG. 2 graphically illustrates it.

TABLE 4

|  | 1 Week from SE Inoculation (log cfu/g) | 2 Weeks from SE Inoculation (log cfu/g) | 3 Weeks from SE Inoculation (log cfu/g) |
| --- | --- | --- | --- |
| Control Group (Additive Free) | 1.84 | 2.00 | 4.34 |
| Comparative Example 2 (Enzymatically Treated Copra Meal, Mannose-Type) | 1.84 | 2.22 | 2.47 |
| Example 6 (Enzymatically Treated Copra Meal, β-Mannobiose-Type) | 2.74 | 1.60 | 0.80 |

It was revealed that the number of *salmonella* in the both groups, one of which was a group given the feed prepared by supplementing the dry powder yielded in Example 6 and the other was a group given the feed prepared by supplementing the dry powder yielded in Comparative Example 2, were smaller than that in the control group at week three from SE inoculation, so that *salmonella* were reduced in those groups. Particularly, the group given the feed prepared by supplementing the dry powder yielded in Example 6 showed smaller number of *salmonella* than that of the group given the feed prepared by supplementing the dry powder yielded in Comparative Example 2, which indicates that the feed prepared by supplementing the dry powder yielded in Example 6 functions more effectively.

EXAMPLE 8

Animal Test 3, Effect on Infant Chicks of Layers 30 of infant chicks of layers at the age of week seven were divided into three groups in total. The three groups consist of a control group of 10 chicks given a commercial blended feed for commercial broiler chicken (trade name: AMATAKE S, agent free/ITOCHU FEED MILLS Co., Ltd.), a group of 10 chicks given the feed prepared by supplementing 0.1% of the dry powder yielded in Example 6 with the blended feed, and a group of 10 chicks given the feed prepared by supplementing 0.1% of dry powder yielded in Comparative Example 2. The chicks were preliminary raised for one week with continuous feeding and voluntary water-drinking. The chicks were then orally inoculated with *salmonella* (*Salmonella enteritidis* HY-1 strain) by $1.13 \times 10^8$ cfu per a chick. Their cecal content was collected and the number of *salmonella*

(log) in their cecal content with respective groups was examined at weeks one, two, three and four from the *salmonella* inoculation.

Figure 3:
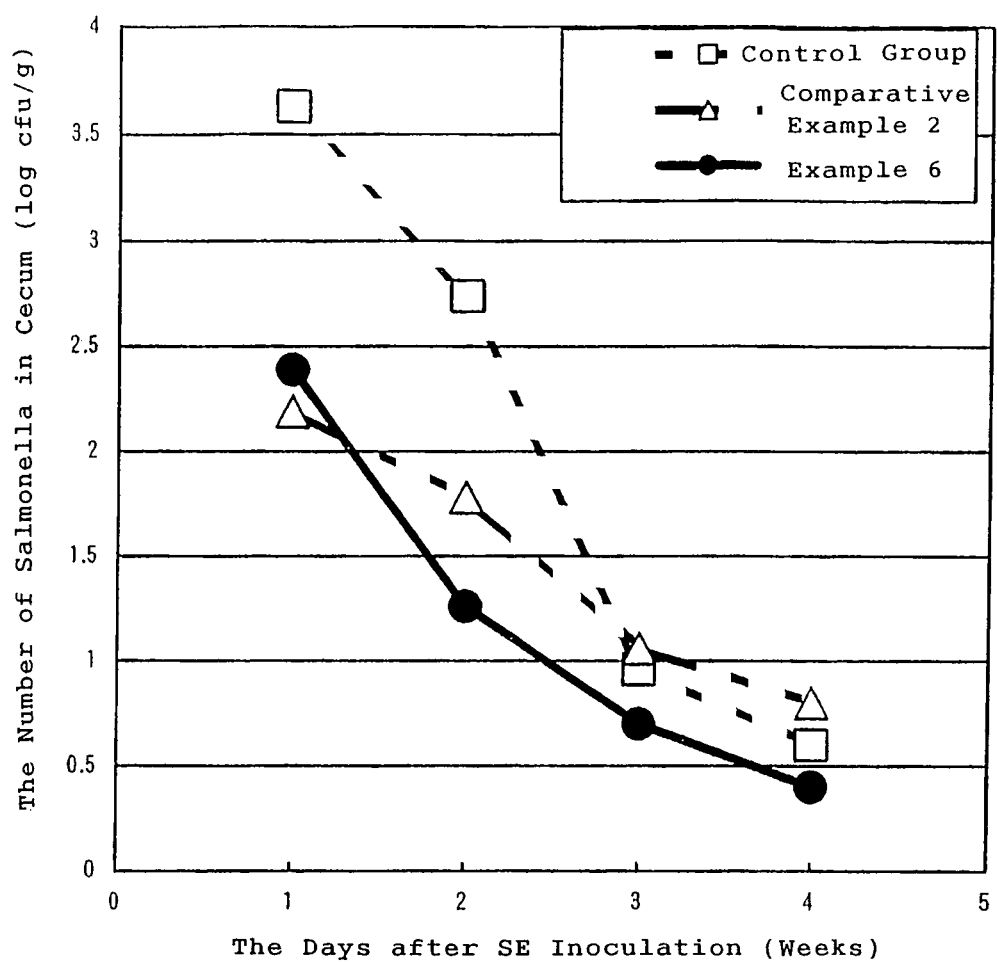
FIG. 3 is a graph showing the number of *salmonella* in cecum with respect to the days after inoculation of *salmonella* in infant chicks of layer at the age of week seven given a feed according to the present invention, a feed according to the Comparative Example 2, and a commercially available feed.

The result is shown in Table 5, while FIG. 3 graphically illustrates it.

TABLE 5

| | 1 Week from SE Inoculation (log cfu/g) | 2 Weeks from SE Inoculation (log cfu/g) | 3 Weeks from SE Inoculation (log cfu/g) | 4 Weeks from SE Inoculation (log cfu/g) |
|---|---|---|---|---|
| Control Group (Additive Free) | 3.63 | 2.74 | 0.96 | 0.60 |
| Comparative Example 2 (Enzymatically Treated Copra Meal, Mannose-Type) | 2.19 | 1.78 | 1.06 | 0.80 |
| Example 6 (Enzymatically Treated Copra Meal, β-Mannobiose-Type) | 2.39 | 1.26 | 0.70 | 0.40 |

It was revealed that the number of *salmonella* in the both groups, one of which was a group given a feed prepared by supplementing the dry powder yielded in Example 6 and the other was a group given a feed prepared by supplementing the dry powder yielded in Comparative Example 2 was smaller than that in the control group at weeks one and two from SE inoculation, so that *salmonella* were reduced in those groups. Particularly, the group given the feed prepared by supplementing the dry powder yielded in Example 6 showed smaller number of *salmonella* than that of the group given the feed prepared by supplementing the dry powder yielded in Comparative Example 2 all through the period, which indicates that the feed prepared by supplementing the dry powder yielded in Example 6 functions more effectively.

INDUSTRIAL APPLICABILITY

According to the present invention, it is possible to provide a β-1,4-mannobiose-containing composition which can inhibit colonization of *salmonella* in animal body and effectively excrete *salmonella* outside the body and the method for producing thereof, a feed additive containing the β-1,4-mannobiose-containing composition, and a feed blended with the β-1,4-mannobiose-containing composition.

The invention claimed is:

1. A method of inhibiting colonization of *Salmonella* in livestock using a β-1,4-mannobiose-containing composition comprising the steps of:
   a) blending the β-1,4-mannobiose-containing composition with a feed to prepare a blended feed; and
   b) feeding the blended feed to livestock or poultry;
   wherein the β-1,4-mannobiose-containing composition is prepared through a reaction of a mannan degrading enzyme and a mannan-containing natural material, the amount of β1,4-mannobiose is at least 3% by weight of the dry matter portion of the β-1,4-mannobiose-containing composition, and the blended feed inhibits the colonization of *Salmonella* in the livestock and poultry.

2. The method of claim 1, wherein the mannan-containing natural material is palm kernel meal, copra meal, or a combination of both.

3. The method of claim 1, wherein the amount of β-1,4-mannobiose is 0.005 to 0.1% by weight of the dry matter portion of said feed of step a).

4. A method of inhibiting colonization of *Salmonella* in livestock using a β-1,4-mannobiose-containing composition comprising the steps of:
   a) blending the β-1,4-mannobiose-containing composition with a feed to prepare a blended feed; and
   b) feeding the blended feed to livestock or poultry;
   wherein the β-1,4-mannobiose-containing composition is prepared through a reaction of a mannan degrading enzyme and a mannan extracted from a mannan-containing natural material, the amount of β-1,4-mannobiose is at least 3% by weight of the dry matter portion of the β-1,4-mannobiose-containing composition, and the blended feed inhibits the colonization of *Salmonella* in the livestock and poultry.

5. The method of claim 4, wherein the amount of β-1,4-mannobiose is 0.005 to 0.1% by weight of the dry matter portion of said feed of step a).

* * * * *